(12) United States Patent
Chen et al.

(10) Patent No.: US 8,766,026 B2
(45) Date of Patent: Jul. 1, 2014

(54) PROCESS FOR THE CONVERSION OF LOWER ALKANES TO AROMATIC HYDROCARBONS

(75) Inventors: Ye Mon Chen, Sugar Land, TX (US); Mahesh Venkataraman Iyer, Houston, TX (US); Karel Martin Kapoun, Sugar Land, TX (US); Ann Marie Lauritzen, Houston, TX (US); Ajay Madhav Madgavkar, Katy, TX (US)

(73) Assignee: Shell Oil Company, Houston, TX (US)

( * ) Notice: Subject to any disclaimer, the term of this patent is extended or adjusted under 35 U.S.C. 154(b) by 204 days.

(21) Appl. No.: 13/105,520

(22) Filed: May 11, 2011

(65) Prior Publication Data

US 2011/0301394 A1 Dec. 8, 2011

Related U.S. Application Data

(60) Provisional application No. 61/333,858, filed on May 12, 2010.

(51) Int. Cl.
*C07C 2/42* (2006.01)
(52) U.S. Cl.
USPC .............................. 585/407; 585/415; 585/418
(58) Field of Classification Search
USPC .......................................... 585/407, 415, 418
See application file for complete search history.

(56) References Cited

U.S. PATENT DOCUMENTS

| | | | |
|---|---|---|---|
| 2,854,402 A * | 9/1958 | Rex | 208/135 |
| 3,751,503 A | 8/1973 | Sampson et al. | |
| 3,827,867 A | 8/1974 | Heinemann et al. | |
| 4,058,452 A | 11/1977 | Lobada | |
| 4,100,218 A | 7/1978 | Chen | |
| 4,120,910 A | 10/1978 | Chu | |
| 4,158,026 A | 6/1979 | Addison | |
| 4,179,474 A | 12/1979 | Beuther et al. | |
| 4,215,231 A | 7/1980 | Raymond | |
| 4,229,602 A | 10/1980 | Brinkmeyer et al. | |
| 4,350,835 A | 9/1982 | Chester et al. | |
| 4,528,412 A | 7/1985 | Steacy | |
| 4,547,205 A | 10/1985 | Steacy | |
| 4,554,393 A | 11/1985 | Liberts et al. | |

(Continued)

FOREIGN PATENT DOCUMENTS

| | | |
|---|---|---|
| CA | 2620480 | 4/2007 |
| EP | 0050021 | 4/1982 |

(Continued)

OTHER PUBLICATIONS

Solymosi, F., et al., "Conversion of Ethane Into Benzene on Mo2C/ZSM-5 Catalyst", Applied Catalysis A: General, Elsevier Science, Amsterdam, NL, vol. 166, No. 1, (1998), pp. 225-235.

(Continued)

*Primary Examiner* — Thuan D Dang

(57) ABSTRACT

A process is provided for producing aromatic hydrocarbons which comprises: (a) contacting a lower alkane feed with a solid particulate aromatic hydrocarbon conversion catalyst in a fixed bed reaction zone to produce aromatic hydrocarbons and other products, whereby the catalyst is at least partially deactivated by the formation of undesirable coke deposits, (b) periodically regenerating the catalyst under regeneration conditions, (c) separating aromatic hydrocarbons from the other products and unreacted lower alkanes, and (d) optionally recycling unreacted lower alkanes to the reaction zone wherein the fixed bed reaction zone additionally comprises a volume of a catalytically inactive solid.

17 Claims, 1 Drawing Sheet

(56) References Cited

U.S. PATENT DOCUMENTS

| | | |
|---|---|---|
| 4,642,402 A | 2/1987 | Jensen |
| 4,677,235 A | 6/1987 | Mowry |
| 4,766,265 A | 8/1988 | Desmond et al. |
| 4,795,845 A | 1/1989 | Martindale et al. |
| 4,806,699 A | 2/1989 | Smith et al. |
| 4,806,700 A | 2/1989 | Martindale |
| 4,808,295 A | 2/1989 | Nemet-Mavrodin |
| 4,849,568 A * | 7/1989 | McCullen et al. ............ 585/407 |
| 4,855,522 A | 8/1989 | Diaz |
| 4,857,498 A | 8/1989 | Dejaifve et al. |
| 4,899,006 A | 2/1990 | Dave et al. |
| 4,912,273 A | 3/1990 | Harandi et al. |
| 4,968,401 A | 11/1990 | Harandi et al. |
| 4,996,381 A | 2/1991 | Pickering, Jr. et al. |
| 5,013,423 A | 5/1991 | Chen et al. |
| 5,019,663 A | 5/1991 | Chou et al. |
| 5,026,937 A | 6/1991 | Bricker ................. 585/415 |
| 5,030,782 A | 7/1991 | Harandi et al. |
| 5,043,506 A | 8/1991 | Crossland |
| 5,053,570 A | 10/1991 | Soto et al. |
| 5,186,908 A | 2/1993 | Nemet-Mavrodin et al. |
| 5,210,350 A | 5/1993 | Solofo et al. |
| 5,227,557 A | 7/1993 | Bournonville et al. |
| 5,258,563 A | 11/1993 | Gosling et al. |
| 5,258,564 A | 11/1993 | Kocval et al. |
| 5,386,071 A | 1/1995 | Kuchar et al. |
| 5,456,822 A | 10/1995 | Marcilly et al. |
| 5,932,777 A | 8/1999 | Sughrue, II et al. |
| 5,936,135 A | 8/1999 | Choudhary et al. |
| 6,143,941 A | 11/2000 | Sharma et al. |
| 6,552,243 B2 | 4/2003 | Allison et al. |
| 6,634,792 B1 | 10/2003 | Gorenne et al. ............ 384/450 |
| 6,635,792 B2 | 10/2003 | Choi et al. |
| 7,019,184 B2 | 3/2006 | Allison et al. |
| 7,186,871 B2 | 3/2007 | Mitchell et al. |
| 7,186,872 B2 | 3/2007 | Juttu et al. |
| 7,276,636 B2 | 10/2007 | Jeanneret |
| 2003/0036670 A1 | 2/2003 | Oh et al. |
| 2003/0135078 A1 | 7/2003 | Lattner et al. ............... 585/639 |
| 2004/0028584 A1 | 2/2004 | Jutta et al. |
| 2005/0143610 A1 | 6/2005 | Mitchell et al. |
| 2006/0287564 A1 | 12/2006 | Choi et al. |
| 2007/0249879 A1 | 10/2007 | Iaccino et al. ............... 585/418 |
| 2008/0093980 A1 | 4/2008 | Stoessel et al. |
| 2008/0154079 A1 | 6/2008 | Ellis et al. .................. 585/407 |
| 2009/0209794 A1 | 8/2009 | Lauritzen et al. ............ 585/415 |
| 2009/0209795 A1 | 8/2009 | Lauritzen et al. ............ 585/417 |
| 2010/0048969 A1 | 2/2010 | Lauritzen et al. |
| 2011/0021853 A1 | 1/2011 | Lauritzen et al. |

FOREIGN PATENT DOCUMENTS

| | | | |
|---|---|---|---|
| EP | 0147111 | 7/1985 | |
| EP | 0244162 | 11/1987 | |
| EP | 244162 | 11/1987 | ............ C07C 2/76 |
| EP | 0269297 | 6/1988 | |
| EP | 0493040 | 7/1992 | |
| EP | 0512912 | 11/1992 | |
| EP | 0905112 | 3/1999 | |
| EP | 1001001 | 5/2000 | |
| GB | 1442850 | 7/1976 | |
| WO | 2007037866 | 4/2007 | |
| WO | 2007048853 | 5/2007 | |
| WO | 2007144324 | 12/2007 | |
| WO | 2009076393 | 6/2009 | |
| WO | 2009105391 | 8/2009 | |
| WO | WO2009105447 | 8/2009 | ............ B01J 29/064 |

OTHER PUBLICATIONS

Choudhary, V.R., et al., Angew Chem. Intl. Engl 36, 1305 (1997), "Synthesis of Aromatic Hydrocarbons from Low-Grade Parafins Using High-Silica Zeolite Catalyst & Metal Carriers", Chemistry Express, vol. 1, pp. 53-56 (1986).

U.S. Appl. No. 61/029,939, filed Feb. 20, 2008, "Process for the Conversion of Ethane to Aromatic Hydrocarbons" (now PCT/US2009/034364, filed Feb. 18, 2009).

U.S. Appl. No. 61/029,478, filed Feb. 18, 2008 (now U.S. Appl. No. 12/371,803, filed Feb. 16, 2009).

U.S. Appl. No. 61/029,481, filed Feb. 18, 2008 (now U.S. Appl. No. 12/371,787, filed Feb. 16, 2009).

* cited by examiner

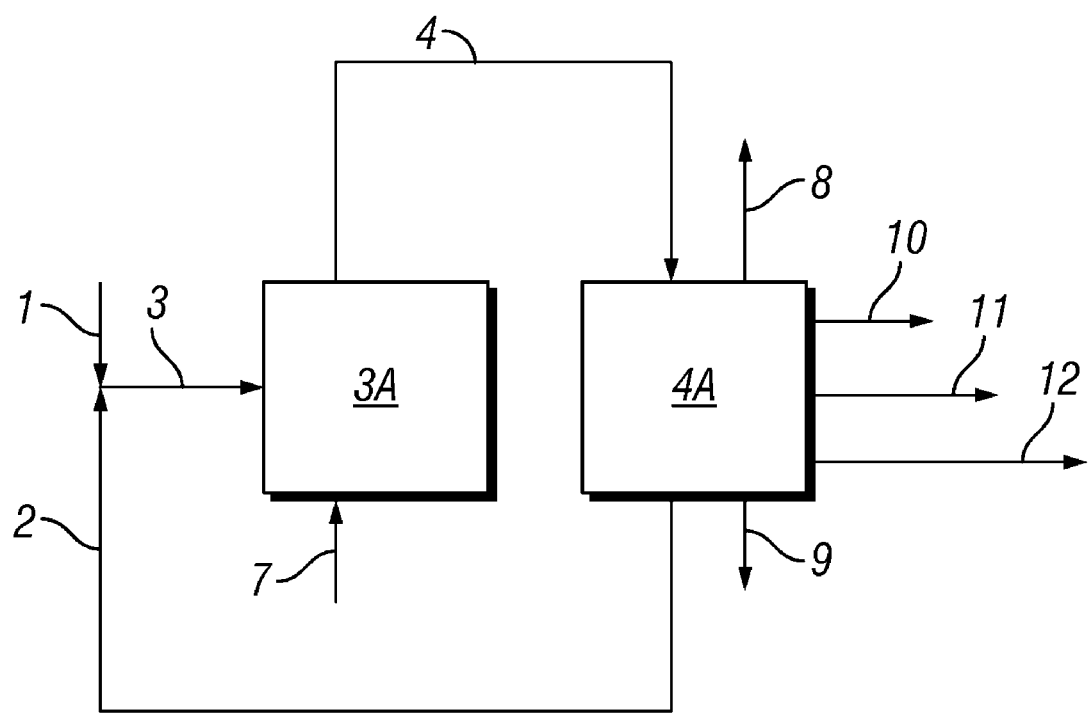

PROCESS FOR THE CONVERSION OF LOWER ALKANES TO AROMATIC HYDROCARBONS

This application claims priority to U.S. Provisional Application No. 61/333,858, filed on May 12, 2010, which is herein incorporated by reference.

FIELD OF THE INVENTION

The present invention relates to a process for producing aromatic hydrocarbons from lower alkanes.

BACKGROUND OF THE INVENTION

There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformates produced through a catalytic reforming process and pyrolysis gasolines produced through a naphtha cracking process, from non-aromatic hydrocarbons using a solvent extraction process.

In an effort to meet growing world demand for key petrochemicals, various industrial and academic researchers have been working for several decades to develop catalysts and processes to make light aromatics, benzene, toluene, xylenes (BTX) from cost-advantaged, light paraffin ($C_1$-$C_4$) feeds. Catalysts devised for this application usually contain a crystalline aluminosilicate (zeolitic) material such as ZSM-5 and one or more metals such as Pt, Ga, Zn, Mo, etc. to provide a dehydrogenation function. Aromatization of ethane and other lower alkanes is thermodynamically favored at high temperature and low pressure without addition of hydrogen to the feed. Unfortunately, these process conditions are also favorable for rapid catalyst deactivation due to formation of undesirable surface coke deposits which block access to the active sites of the catalyst.

One approach to circumvent this rapid deactivation problem is to devise a lower alkane aromatization process featuring one or more catalyst beds in which the catalyst bed(s) are cycled rapidly and continuously between reaction conditions suitable for aromatization to take place and regeneration conditions suitable for removing the accumulated coke from the catalyst to restore activity.

Due to the highly endothermic nature of the alkane aromatization reaction, there is a need to maintain a heat balance between the reaction and regeneration steps of the cycle.

SUMMARY OF THE INVENTION

The invention relates to a fixed bed process for aromatization of lower alkanes utilizing an alkane aromatization catalyst diluted with a second, inert solid material. The present invention calls for meeting the need for heat balance, adequate heat transfer, and satisfying activity requirements, by incorporating a catalytically inactive solid with similar or improved specific heat and thermal conductivity relative to the catalyst material in the catalyst bed.

A process is provided for producing aromatic hydrocarbons which comprises: (a) contacting a lower alkane feed with a solid particulate aromatic hydrocarbon conversion catalyst in a fixed bed reaction zone to produce aromatic hydrocarbons and other products, whereby the catalyst is at least partially deactivated by the formation of undesirable coke deposits, (b) periodically regenerating the catalyst under regeneration conditions, (c) separating aromatic hydrocarbons from the other products and unreacted lower alkanes, and (d) optionally recycling unreacted lower alkanes to the reaction zone wherein the fixed bed reaction zone additionally comprises a volume of a catalytically inactive solid.

In one embodiment of the present invention, the specific heat of the catalytically inactive solid is at least about 0.2 Btu/(lb-° R) (about 0.8 kJ/(kg-° K)). In another embodiment, the specific heat of the catalytically inactive solid is from about 0.2 to about 0.4 Btu/(lb-° R) (about 0.8 to about 1.7 kJ/(kg-° K)) at the temperature of operation.

"At the temperature of operation" relates to the changes that may occur in specific heat when the temperature is increased from ambient to the reaction temperature (for example, the specific heat of DENSTONE® 80 bed support media below is about 1.05 at ambient temperature and 1.18 in the range of the reaction temperature of this invention). The temperature of operation is generally about 200 to about 1000° C., preferably from about 300 to about 850° C., most preferably from about 575 to about 750° C.

BRIEF DESCRIPTION OF THE DRAWINGS

FIG. 1 is a flow diagram which illustrates a process scheme for producing aromatics (benzene and higher aromatics) from lower alkanes.

DETAILED DESCRIPTION OF THE INVENTION

The present invention is a process for producing aromatic hydrocarbons which comprises bringing a hydrocarbon feedstock generally containing at least about 50 percent by weight of lower alkanes and a catalyst composition suitable for promoting the reaction of lower alkanes to aromatic hydrocarbons such as benzene into contact at a temperature of about 200 to about 1000° C., preferably from about 300 to about 850° C., most preferably from about 575 to about 750° C. and a pressure of about 0.01 to about 0.5 MPa. The primary desired products of the process of this invention are benzene, toluene and xylene.

The hydrocarbons in the feedstock may include ethane, propane, butane, and/or $C_{5+}$ alkanes or any combination thereof. Preferably, the majority of the feedstock is ethane and propane. The feedstock may contain in addition other open chain hydrocarbons containing between 3 and 8 carbon atoms as coreactants. Specific examples of such additional coreactants are propylene, isobutane, n-butenes and isobutene. The hydrocarbon feedstock preferably contains at least about 30 percent by weight of $C_{2-4}$ hydrocarbons, more preferably at least about 50 percent by weight.

This invention relates to a processing scheme for producing benzene (and other aromatics) from a mixed lower alkane stream which may contain $C_2$, $C_3$, $C_4$ and/or $C_{5+}$ alkanes, for example an ethane/propane/butane-rich stream derived from natural gas, refinery or petrochemical streams including waste streams. Examples of potentially suitable feed streams include (but are not limited to) residual ethane and propane from natural gas (methane) purification, pure ethane, propane and butane streams (also known as Natural Gas Liquids) co-produced at a liquefied natural gas site, $C_2$-$C_5$ streams from associated gases co-produced with crude oil production, unreacted ethane "waste" streams from steam crackers, and the $C_1$-$C_3$ byproduct stream from naphtha reformers. The lower alkane feed may be deliberately diluted with relatively inert gases such as nitrogen and/or with various light hydrocarbons and/or with low levels of additives needed to improve catalyst performance.

The alkane aromatization reaction is highly endothermic and requires a great amount of heat. At high temperatures, the aromatization catalysts rapidly deactivate due to formation of undesirable surface coke deposits which block access to the active sites of the catalyst. The reaction zone in the process of the present invention may be rapidly and continuously cycled between reaction conditions and regeneration conditions, to burn off or otherwise remove the coke from the catalyst to restore its activity. Thus, the process in the regeneration step is exothermic and generates heat.

It is important that an equilibrium be established between the gain and loss of heat in the reaction system, i.e., a heat balance must be established. In the present invention, this is particularly important because of the endothermicity of the reaction step, the exothermicity of the regeneration step and the expensive heat exchange system that would be required at both the reaction and regeneration steps if this heat balance is not established.

A heat balance could be established by maintaining a high inventory of solid catalyst particles in the reaction system. This would work because (a) the excess amount of catalyst solids may absorb the heat during coke burn in the regeneration section preventing the temperature to rise to levels that could be detrimental to the catalyst (b) the excess hot solids may also provide all the heat necessary for the endothermic reactions. However, the aromatization catalysts are expensive and taking this approach would dramatically increase the cost of the process.

The present invention provides a solution to the problem of establishing heat balance in the reaction system. Instead of using a large excess of catalyst particles, the desired amount of catalyst necessary for the size of the reactor and the amount of feed may be utilized. The catalyst particles may then be diluted by the addition of particles of a catalytically inactive solid which will assist in transferring heat from the regeneration step to the reaction step without using heat exchange systems for both steps.

The ratio of the mass of inert particles to the mass of the catalyst particles may be at least about 1:6 because less inert material than that would provide very little value in terms of enhanced heat transfer. Generally, the ratio may be as much as about 6:1. No more than this may generally be used because the amount of catalyst may be inadequate for the reaction. Preferably, the ratio may be from about 0.4:1 to about 2.5:1 to achieve good heat transfer and sufficient reaction.

Best results will be achieved when the catalytically inactive solid has about the same or improved heat transfer properties relative to the catalyst. Specific heat capacity (also known simply as specific heat) is an important characteristic for the choice of the catalytically inactive solid.

It is preferred that the specific heat capacity of the catalytically inactive solid be about the same as that of the catalyst itself or improved (greater). Preferably, the specific heat of the catalytically inactive solid particles may be at least about 0.2 Btu/(lb-° R) (0.8 kJ/(kg-° K)) at the temperature of operation, more preferably from about 0.2 to about 0.4 Btu/(lb-° R) (from about 0.8 to about 1.7 kJ/(kg-° K)), most preferably from about 0.25 to about 0.35 Btu/lb/OR Btu/(lb-° R) (from about 1.04 to about 1.5 kJ/(kg-° K) because higher specific heats result in lower amount of solids in the system: either circulation, or inventory. Also, the specific heat ranges are preferred because they are close to that of the supported catalyst used in the invention.

Improved results may be achieved if the thermal characteristics of the catalytically inactive solid are improved in relation to those of the catalyst.

The catalytically inactive solid may be selected from alumina, silica, titania, clays, alkali oxides, alkaline earth oxides, bakelite, pyrex glass, limestone, gypsum, silicon carbide, and other refractory materials known to the practitioners of art and/or combinations thereof. Fixed bed support media such as DENSTONE® bed support media may be used in the present invention. For example, DENSTONE® 80 bed support media has a specific heat capacity of 0.28 Btu/(lb-° R) (1.18 kJ/(kg-° K)) at the temperature of operation. A typical aromatization catalyst such as the one described in U.S. Patent Application Publication 2009/0209795 discussed below has a specific heat capacity of 0.28 Btu/(lb-° R) (1.17 kJ/(kg-° K)) at the temperature of operation. These two materials would match up well for use in the present invention. Other catalytically inactive solids which should also work well are shown in Table 1 below with their specific heats ($C_p$) at a temperature of from 600° C. to 700° C.

TABLE 1

| Material | Cp (Btu/lb/degR) | Cp (kJ/kg/degK) |
|---|---|---|
| Denstone 80 | 0.283 | 1.18 |
| Quartz | 0.28 | 1.17 |
| Concrete | 0.22 | 0.92 |
| Silicate Glass | 0.26 | 1.09 |
| Limestone | 0.285 | 1.19 |
| Silica | 0.31 | 1.30 |
| Alumina | 0.285 | 1.19 |
| Gypsum | 0.275 | 1.15 |
| CaO | 0.225 | 0.94 |
| Titania | 0.223 | 0.93 |
| MgO | 0.31 | 1.30 |
| $K_2O$ | 0.275 | 1.15 |
| $Na_2O$ | 0.355 | 1.49 |

The particle size of the inert material may vary depending upon the type of reactor used. Generally, the particle size of the inert material may be in the same range as the particle size of the catalyst particles.

Any one of a variety of catalysts may be used to promote the reaction of lower alkanes to aromatic hydrocarbons. One such catalyst is described in U.S. Pat. No. 4,899,006 which is herein incorporated by reference in its entirety. The catalyst composition described therein comprises an aluminosilicate having gallium deposited thereon and/or an aluminosilicate in which cations have been exchanged with gallium ions. The molar ratio of silica to alumina is at least 5:1.

Another catalyst which may be used in the process of the present invention is described in EP 0 244 162. This catalyst comprises the catalyst described in the preceding paragraph and a Group VIII metal selected from rhodium and platinum. The aluminosilicates are said to preferably be MFI or MEL type structures and may be ZSM-5, ZSM-8, ZSM-11, ZSM-12 or ZSM-35.

Other catalysts which may be used in the process of the present invention are described in U.S. Pat. Nos. 7,186,871 and 7,186,872, both of which are herein incorporated by reference in their entirety. The first of these patents describes a platinum containing ZSM-5 crystalline zeolite synthesized by preparing the zeolite containing the aluminum and silicon in the framework, depositing platinum on the zeolite and calcining the zeolite. The second patent describes such a catalyst which contains gallium in the framework and is essentially aluminum-free.

Additional catalysts which may be used in the process of the present invention include those described in U.S. Pat. No. 5,227,557, hereby incorporated by reference in its entirety. These catalysts contain an MFI zeolite plus at least one noble metal from the platinum family and at least one additional metal chosen from the group consisting of tin, germanium, lead, and indium.

One preferred catalyst for use in this invention is described in U.S. Patent Application Publication No. 2009/0209795, which is hereby incorporated by reference in its entirety. This publication describes a catalyst comprising: (1) about 0.005 to about 0.1% wt (% by weight) platinum, basis the metal, preferably about 0.01 to about 0.05% wt, (2) an amount of an attenuating metal selected from the group consisting of tin, lead, and germanium, which is no more than 0.02% wt less than the amount of platinum, preferably not more than about 0.2% wt of the catalyst, basis the metal; (3) about 10 to about 99.9% wt of an aluminosilicate, preferably a zeolite, basis the aluminosilicate, preferably about 30 to about 99.9% wt, preferably selected from the group consisting of ZSM-5, ZSM-11, ZSM-12, ZSM-23, or ZSM-35, preferably converted to the H+ form, preferably having a $SiO_2/Al_2O_3$ molar ratio of from about 20:1 to about 80:1, and (4) a binder, preferably selected from silica, alumina and mixtures thereof.

Another preferred catalyst for use in this invention is described in PCT Publication No. WO 2009/105447, which is hereby incorporated by reference in its entirety. The publication describes a catalyst comprising: (1) about 0.005 to about 0.1% wt (% by weight) platinum, basis the metal, preferably about 0.01 to about 0.06% wt, most preferably about 0.01 to about 0.05% wt, (2) an amount of iron which is equal to or greater than the amount of the platinum but not more than about 0.50% wt of the catalyst, preferably not more than about 0.20% wt of the catalyst, most preferably not more than about 0.10% wt of the catalyst, basis the metal; (3) about 10 to about 99.9% wt of an aluminosilicate, preferably a zeolite, basis the aluminosilicate, preferably about 30 to about 99.9% wt, preferably selected from the group consisting of ZSM-5, ZSM-11, ZSM-12, ZSM-23, or ZSM-35, preferably converted to the H+ form, preferably having a $SiO_2/Al_2O_3$ molar ratio of from about 20:1 to about 80:1, and (4) a binder, preferably selected from silica, alumina and mixtures thereof.

Another preferred catalyst for use in this invention is described in U.S. Patent Application Publication No. 2009/0209794, which is hereby incorporated by reference in its entirety. This application describes a catalyst comprising: (1) about 0.005 to about 0.1 wt % (% by weight) platinum, basis the metal, preferably about 0.01 to about 0.05% wt, most preferably about 0.02 to about 0.05% wt, (2) an amount of gallium which is equal to or greater than the amount of the platinum, preferably no more than about 1 wt %, most preferably no more than about 0.5 wt %; (3) about 10 to about 99.9 wt % of an aluminosilicate, preferably a zeolite, basis the aluminosilicate, preferably about 30 to about 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from about 20:1 to about 80:1, and (4) a binder, preferably selected from silica, alumina and mixtures thereof.

A hydrodealkylation reaction, which involves the reaction of toluene, xylenes, ethylbenzene, and higher aromatics with hydrogen to strip alkyl groups from the aromatic ring, may be incorporated to produce additional benzene and light ends including methane and ethane which are separated from the benzene. This step substantially increases the overall yield of benzene and thus is highly advantageous.

Both thermal and catalytic hydrodealkylation processes are known in the art. Thermal dealkylation may be carried out as described in U.S. Pat. No. 4,806,700, which is herein incorporated by reference in its entirety. Hydrodealkylation operation temperatures in the described thermal process may range from about 500 to about 800° C. at the inlet to the hydrodealkylation reactor. The pressure may range from about 2000 kPa to about 7000 kPa. A liquid hourly space velocity in the range of about 0.5 to about 5.0 based upon available internal volume of the reaction vessel may be utilized. Due to the exothermic nature of the reaction, it is often required to perform the reaction in two or more stages with intermediate cooling or quenching of the reactants. Two or three or more reaction vessels may therefore be used in series. The cooling may be achieved by indirect heat exchange or interstage cooling. When two reaction vessels are employed in the hydrodealkylation zone, it is preferred that the first reaction vessel be essentially devoid of any internal structure and that the second vessel contain sufficient internal structure to promote plug flow of the reactants through a portion of the vessel.

Alternatively, the hydrodealkylation zone may contain a bed of a solid catalyst such as the catalyst described in U.S. Pat. No. 3,751,503, which is herein incorporated by reference in its entirety. Another possible catalytic hydrodealkylation process is described in U.S. Pat. No. 6,635,792, which is herein incorporated by reference in its entirety. This patent describes a hydrodealkylation process carried out over a zeolite-containing catalyst which also contains platinum and tin or lead. The process is preferentially performed at temperatures ranging from about 250° C. to about 600° C., pressures ranging from about 0.5 MPa to about 5.0 MPa, liquid hydrocarbon feed rates from about 0.5 to about 10 hr−1 weight hourly space velocity, and molar hydrogen/hydrocarbon feedstock ratios ranging from about 0.5 to about 10.

EXAMPLES

The examples provided below are intended to illustrate but not limit the scope of the invention.

Example 1

The details of the preparation methods, fixed-bed lab-scale testing procedures, and comparative initial performance results obtained under ethane aromatization conditions with a Pt/Ga catalyst made on ZSM-5/alumina extrudate particles are described below. In the reference runs, fresh Pt/Ga catalyst charges were loaded "as is," without any solid diluent. In addition, a charge consisting of 40% v of the Pt/Ga catalyst (specific heat—1.17 kJ/(kg-° K) (0.28 Btu/(lb-° R)) and 60% v of a commercially-available solid inert silica/alumina material (Denstone® 80 ⅛-inch spheres available from Saint-Gobain N or Pro; specific heat—1.18 kJ/(kg-° K) (0.28 Btu/(lb-° R)) was tested under the same conditions.

The catalyst used in these tests was prepared on samples of an extrudate material containing 80% wt of CBV 3014E ZSM-5 zeolite (30:1 molar $SiO_2$:$Al_2O_3$ ratio; available from Zeolyst International) and 20% wt of alumina binder. This cylindrical extrudate had a diameter of 1.6 mm. The samples were calcined in air up to 425° C. for 1 hr to remove moisture prior to use in catalyst preparation.

Metals were deposited on 100-g samples of the ZSM-5 extrudate by first combining appropriate amounts of stock solutions containing tetraammine platinum nitrate and gallium (III) nitrate, diluting this mixture with deionized water to a volume just sufficient to fill the pores of the extrudate, and impregnating the extrudate with the solution at room temperature and atmospheric pressure. Impregnated samples were aged at room temperature for 2-3 hrs and then dried overnight at 100° C. The target Pt and Ga levels on the catalyst were 0.025% wt and 0.15% wt, respectively.

The catalyst samples described above were tested "as is," without crushing. Performance tests A, B, and C were conducted with undiluted catalyst. For each of these three tests, a 15-cc charge of catalyst was loaded into a quartz tube (1.40 cm inner diameter) and positioned in a three-zone furnace connected to an automated gas flow system. Performance test D was conducted with catalyst plus solid, inert diluent. For performance test D, the charge consisted of a physical mixture of 6 cc of catalyst plus 9 cc of Denstone® 80 ⅛-inch diameter inert aluminum silicate spheres, available from Saint-Gobain N or Pro.

Prior to performance testing, all catalyst charges were pretreated in situ at atmospheric pressure as follows:
(a) calcination with air at 60 L/hr, with reactor wall temperature ramped from 25 to 510° C. in 12 hrs, held at 510° C. for 4-8 hrs, ramped from 510 to 630° C. in 1 hr, and then held at 630° C. for 30 min;
(b) nitrogen purge at 60 L/hr, 630° C. for 20 min;
(c) reduction with hydrogen at 60 L/hr, 630° C. for 30 min.

At the end of the pretreatment, 100% ethane feed was introduced at 1000 GHSV (with respect to catalyst) and atmospheric pressure with the reactor wall temperature maintained at 630° C. The total reactor outlet stream was sampled and analyzed by an online gas chromatography system two minutes after ethane feed addition. Based on the composition data obtained from the gas chromatographic analysis the initial ethane conversion was computed according to the following formula:

ethane conversion(%)=100×(100−% wt ethane in outlet stream)/(% wt ethane in feed). The results of performance tests A, B, C and D, conducted as described above, are presented in Table 2. Average values and standard deviations for the ethane conversion and product selectivities obtained in tests A, B and C are also provided in Table 2. Comparison of the results in Table 2 indicates that 40/60 (v/v) dilution of the catalyst with the Denstone® 80 inert particles did not adversely affect initial activity, benzene yield, or total aromatics yield under the ethane aromatization test conditions used here. Thus, less catalyst produced similar results in test D.

Example 2

In this example, ethane is converted to aromatic hydrocarbons using the process configuration shown in FIG. 1. 25 tonnes/hr (tph) of stream (1), which primarily constitutes ethane feed (including minor amounts of methane, propane and butane), is mixed with 37 tph of recycle stream (2) that consists primarily of ethane and other hydrocarbons which may include ethylene, propane, propylene, methane, butane and some hydrogen. The total feed amounting to 62 tph (Stream 3) is introduced to the ethane aromatization reactor (3A). The unconverted reactants as well as the products leave the reactor (3A) via stream (4) and are fed to the separation system (4A). The unconverted reactants and light hydrocarbons are recycled back (stream 2) to the reactor while the separation system (4A) yields 8 tph fuel gas (stream 8—predominantly methane and hydrogen), 2 tph $C_{9+}$ liquid products (stream 9), 9 tph benzene (stream 10), 5 tph toluene (stream 11) and 1 tph xylenes (stream 12).

The aromatization reactor system (3A) may be a fluidized bed, moving bed or a cyclic fixed bed design. Here in this specific example the cyclic fixed bed design is used, in which particles of the catalyst, used in Example 1, cycle between reaction conditions where aromatization of the feed takes place and regeneration conditions where a hot hydrogen containing stripping gas (stream 7) is used. In this illustrative example, the reactor bed system (3A) operates under reaction conditions of about 1 atmosphere pressure and at a temperature of 630° C.; and under regeneration conditions at a temperature of 730° C. and 1 atmosphere.

The ethane to aromatic conversion process is endothermic and reactor system (3A) requires 71,000 MJ/hr heat energy. In addition, the spent catalyst is prone to deactivation due to coke deposition and must be regenerated subsequently via hot hydrogen containing stripping gas in a regeneration step. The endothermic heat of 71,000 MJ/hr can be provided via interstage heat exchangers (not shown) thus making the system very expensive. An alternative approach, would be to use the heat capacity of the bulk solid catalysts to provide heat for the

TABLE 2

| Performance test | A | B | C | Average Values, Tests A-C | Standard Deviations, Tests A-C | D |
|---|---|---|---|---|---|---|
| Amount of Catalyst, cc | 15 | 15 | 15 | | | 6 |
| Amount of Inert Diluent, cc | 0 | 0 | 0 | | | 9 |
| Ethane conversion, % | 46.83 | 46.24 | 46.72 | 46.60 | 0.31 | 47.90 |
| Reactor Outlet Gas Composition, % wt | | | | | | |
| Hydrogen | 4.16 | 4.14 | 4.10 | 4.13 | 0.03 | 4.26 |
| Methane | 8.20 | 7.80 | 8.31 | 8.10 | 0.27 | 8.50 |
| Ethylene | 5.09 | 5.17 | 5.23 | 5.16 | 0.07 | 5.26 |
| Ethane | 53.17 | 53.76 | 53.28 | 53.40 | 0.31 | 52.10 |
| Propylene | 0.67 | 0.68 | 0.68 | 0.68 | 0.01 | 0.66 |
| Propane | 0.72 | 0.74 | 0.72 | 0.73 | 0.01 | 0.69 |
| C4 | 0.15 | 0.17 | 0.16 | 0.16 | 0.01 | 0.15 |
| C5 | 0.01 | 0.02 | 0.01 | 0.01 | 0.01 | 0.02 |
| Benzene | 15.15 | 14.70 | 15.14 | 15.00 | 0.26 | 14.97 |
| Toluene | 7.91 | 7.96 | 7.97 | 7.95 | 0.03 | 7.67 |
| C8 Aromatics | 1.51 | 1.61 | 1.53 | 1.55 | 0.05 | 1.47 |
| C9+ Aromatics | 3.26 | 3.25 | 2.87 | 3.13 | 0.22 | 4.25 |
| Total Aromatics | 27.83 | 27.51 | 27.51 | 27.62 | 0.18 | 28.36 | reaction, by pre-heating the catalysts to a higher temperature such as 730° C. which eliminates the need for interstage process heaters.

The quantity of the solid catalyst particles required for the reaction, determined by the gas hourly space velocity is 39 tonnes in this example. Now these hot catalyst particles act as heat transfer particulate material between the regeneration step and the endothermic reaction step. For these hot catalyst particles to provide sufficient heat during the endothermic reaction step, the solid catalyst inventory in the reactor system needs to be increased to 49 tonnes in this example. This increased solid catalyst inventory would now be able to provide all of the 71,000 MJ/hr of endothermic heat duty to the reactor (3A) operating at 630° C.

In another modification to the system (which is the preferred improvement proposed in this invention), inert solids (such as Denstone®-80 support material) are used as heat transfer particulates and are mixed with the catalyst particles. Denstone®-80 bed support media is described above. These inert particles are significantly less expensive than the catalyst particles but they have the same or similar heat transfer properties, a specific heat of 0.28 Btu/(lb-° R) (1.17 kJ/(kg-° K). The catalyst solid inventory is kept the same to maintain the same contact time between the feed and the catalyst. This corresponds to a catalyst inventory of 39 tonnes as mentioned earlier. Thus, in this example, a mixture of 39 tonnes of catalyst and 10 tonnes of inert solids, totaling to 49 tonnes of the solid mixture, is loaded in the fixed bed the reactor system. The solid particulate mixture is able to transfer all the heat from the regeneration step to the reaction step while limiting temperature rise and catalyst sintering. The heat transfer properties of the combined catalyst-Denstone®-80 solid particulate mixture are identical or similar to that of the catalyst particulates. This can be seen from the chemical compositions of the solid particulate system as shown in tables 3, 4 and 5 below (Fr.=fraction).

This mode of operation results in lower catalyst loading and hence reduction in catalyst inventory and hence losses.

TABLE 3

Typical chemical composition of the catalyst system

| Catalyst | Wt. Fr. % |
|---|---|
| $SiO_2$ | 75.7% |
| $Al_2O_3$ | 24.3% |

TABLE 4

Typical chemical composition of the Denstone ®-80 inerts

| Denstone 80 | wt. fr. % |
|---|---|
| $SiO_2$ | 66.1 |
| $Al_2O_3$ | 26.85 |
| $TiO_2$ | 1.25 |
| $K_2O$ | 2.43 |
| $Na_2O$ | 2.51 |
| CaO | 0.61 |
| MgO | 0.25 |

TABLE 5

Typical chemical composition of catalyst and Denstone ®-80 inert mixture

| Catalyst-Inert Mixture | wt. fr. (%) |
|---|---|
| $SiO_2$ | 73.8 |
| $Al_2O_3$ | 24.8 |
| $TiO_2$ | 0.3 |
| $K_2O$ | 0.5 |
| $Na_2O$ | 0.5 |
| CaO | 0.1 |
| MgO | 0.1 |

We claim:

1. A process for producing aromatic hydrocarbons which comprises:
   (a) contacting a lower alkane feed, wherein the majority of the feed is ethane and propane, with a solid particulate aromatic hydrocarbon conversion catalyst in a fixed bed reaction zone to produce aromatic hydrocarbons and other products from ethane and propane, whereby the catalyst is at least partially deactivated by the formation of undesirable coke deposits,
   (b) periodically regenerating the catalyst under regeneration conditions,
   (c) separating aromatic hydrocarbons from the other products and unreacted lower alkanes, and
   (d) optionally recycling unreacted lower alkanes to the reaction zone
   wherein the fixed bed reaction zone additionally comprises a volume of a catalytically inactive solid particles interspersed with the catalyst particles to establish a heat balance between the reaction step and the regeneration step.

2. The process of claim 1 wherein the ratio of the volume or the weight of the catalytically inactive solid to the volume or the weight of the catalyst particles is from 1:6 to 6:1.

3. The process of claim 2 wherein the ratio of the volume or the weight of the catalytically inactive solid to the volume or the weight of the catalyst particles is from 0.4:1 to 2.5:1.

4. The process of claim 1 wherein the specific heat of the catalytically inactive solid is at least 0.2 Btu/(lb-° R) (0.8 kJ/(kg-° K)) at the temperature of operation.

5. The process of claim 4 wherein the specific heat of the catalytically inactive solid is from 0.2 to 0.4 Btu/(lb-° R)(0.8 to 1.7 kJ/(kg-° K)) at the temperature of operation.

6. The process of claim 5 wherein the specific heat of the catalytically inactive solid is from 1.04 to 1.5 kJ/(kg-° K).

7. The process of claim 1 wherein the catalytically active solid is selected from the group consisting of alumina, silica, titania, clays, alkali oxides, alkaline earth oxides, Bakelite, pyrex glass, limestone, gypsum, silicon carbide, and combinations thereof.

8. The process of claim 1 wherein the aromatic hydrocarbons comprise benzene.

9. The process of claim 1 wherein the aromatic hydrocarbons comprise benzene and toluene.

10. The process of claim 1 wherein the aromatic hydrocarbons comprise benzene, toluene and xylene.

11. A process for producing aromatic hydrocarbons which comprises:
   (a) contacting a lower alkane feed, comprising C1 to C3 alkanes, with a solid particulate aromatic hydrocarbon conversion catalyst in a fixed bed reaction zone to produce aromatic hydrocarbons and other products from C1 to C3 alkanes, whereby the catalyst is at least partially deactivated by the formation of undesirable coke deposits, (b) periodically regenerating the catalyst under regeneration conditions, (c) separating aromatic hydrocarbons from the other products and unreacted lower alkanes, and (d) optionally recycling unreacted lower alkanes to the reaction zone wherein the fixed bed reaction zone additionally comprises a volume of a catalytically inactive solid particles interspersed with the catalyst particles to establish a heat balance between the reaction step and the regeneration step.

12. The process of claim 11 wherein the ratio of the volume or the weight of the catalytically inactive solid to the volume or the weight of the catalyst particles is from 1:6 to 6:1.

13. The process of claim 12 wherein the ratio of the volume or the weight of the catalytically inactive solid to the volume or the weight of the catalyst particles is from 0.4:1 to 2.5:1.

14. The process of claim 11 wherein the specific heat of the catalytically inactive solid is at least 0.2 Btu/(lb-° R) (0.8 kJ/(kg-° K)) at the temperature of operation.

15. The process of claim 14 wherein the specific heat of the catalytically inactive solid is from 0.2 to 0.4 Btu/(lb-° R)(0.8 to 1.7 kJ/(kg-° K)) at the temperature of operation.

16. The process of claim 11 wherein the catalytically active solid is selected from the group consisting of alumina, silica, titania, clays, alkali oxides, alkaline earth oxides, Bakelite, pyrex glass, limestone, gypsum, silicon carbide, and combinations thereof.

17. The process of claim 11 wherein the aromatic hydrocarbons comprise benzene.

* * * * *